United States Patent
Chang

(12) 
(10) Patent No.: US 6,197,298 B1
(45) Date of Patent: *Mar. 6, 2001

(54) MODIFIED BINDING MOLECULES SPECIFIC FOR T LYMPHOCYTES AND THEIR USE AS IN VIVO IMMUNE MODULATORS IN ANIMALS

(75) Inventor: Tse Wen Chang, Houston, TX (US)

(73) Assignee: Tanox, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/035,723

(22) Filed: Mar. 23, 1993

Related U.S. Application Data

(63) Continuation-in-part of application No. 07/993,291, filed on Dec. 18, 1992, now Pat. No. 5,872,222, and a continuation-in-part of application No. 07/981,276, filed on Nov. 25, 1992, now Pat. No. 6,129,916, which is a continuation-in-part of application No. 07/926,566, filed on Aug. 6, 1992, now abandoned, which is a continuation-in-part of application No. 07/819,449, filed on Jan. 10, 1992, now abandoned, which is a continuation-in-part of application No. 07/688,000, filed on Apr. 19, 1991, now abandoned.

(51) Int. Cl.⁷ .................................................. A61K 39/40
(52) U.S. Cl. ..................................... 424/179.1; 424/178.1; 424/480; 530/388.75; 530/389.6; 530/387.1
(58) Field of Search ........................... 530/388.75, 389.6, 530/387.1; 424/450, 178.1, 179.1

(56) References Cited

U.S. PATENT DOCUMENTS 4,867,973 * 9/1989 Goero et al. ...................... 424/85.91

FOREIGN PATENT DOCUMENTS

| 3242389 | 5/1989 | (AU) . |
| 6623590 | 5/1991 | (AU) . |
| 0336379 | 4/1989 | (EP) . |
| WO8912458 | 12/1989 | (WO) . |
| WO9006758 | 6/1990 | (WO) . |
| WO9013281 | 11/1990 | (WO) . |
| WO9013316 | 11/1990 | (WO) . |
| WO9103493 | 3/1991 | (WO) . |
| WO9206193 | 4/1992 | (WO) . |
| WO9207878 | 5/1992 | (WO) . |
| WO9213562 | 8/1992 | (WO) . |

OTHER PUBLICATIONS

Raitt *Immunology* Gower Medical Publishing 1985 pg 8.7 fig 8.19.*
Williams et al J. Immunology 135(4):2249–2255 1985.*
Geppert et al J. Immunology 138(6):1660–1666 1987.*
Verwilghen et al Immunology 72:269–276 1991.*
Harris et al Tibtech 11:42–46 1993.*
Waldmann Science 252:1657–1662 1992.*
Paul, *Fundamental Immunology* p. 364 (1989) Raven Press.*
Harlow et al. *Antibodies: a laboratory manual*, Cold Spring Harbor Press 1988.*
Martin J.I. 136 3282 1986.*

* cited by examiner

*Primary Examiner*—Jyothsna Venkat
*Assistant Examiner*—T. D. Wessendorf
(74) *Attorney, Agent, or Firm*—Eric R. Mirabel

(57) ABSTRACT

Several forms of immunoregulatory substances are derived from monoclonal antibodies (MAbs) that are specific for a T cell surface antigen, such as CD3, TCR, CD4, or CD8 on T cells. The substances include: a mixture of $F(ab')_2$ fragments (or other divalent binding molecules which lack Fc) which each bind noncompetitively to different monovalent antigenic epitopes on the same antigen; the $F(ab')_2$ fragment (or other divalent binding molecules which lack Fc) of a bispecific antibody which has each of its binding sites derived from one of the two MAbs that bind noncompetitively to monovalent antigenic epitopes on the same antigen; a conjugate including a polymeric backbone, such as polyethylene glycol ("PEG"), cellulose, dextran, agarose, or an amino acid copolymer or a liposome, that is coupled with the binding molecules, e.g., Fv, Fab, or $F(ab')_2$, which bind noncompetitively to monovalent antigenic epitopes on the same antigen.

8 Claims, No Drawings

MODIFIED BINDING MOLECULES SPECIFIC FOR T LYMPHOCYTES AND THEIR USE AS IN VIVO IMMUNE MODULATORS IN ANIMALS

RELATED APPLICATIONS

This application is a continuation-in-part of U.S. application Ser. No. 07/993,291, filed Dec. 18, 1992 now U.S. Pat. No. 5,872,222 U.S. application Ser. No. 07/981,276, filed Nov. 25, 1992, now U.S. Pat. No. 6,129,916, which is a continuation-in-part of U.S. application Ser. No. 07/926,566, filed Aug. 6, 1992 (abandoned) and U.S. application Ser. No. 07/819,449, filed Jan. 10, 1992 (abandoned), which is a continuation-in-part of U.S. application Ser. No. 07/688,000, filed Apr. 19, 1991 (abandoned).

FIELD OF INVENTION

The invention relates to binding molecules, such as antibody fragments and immunoconjugates, for modulating the immune system by inducing specifically the polyclonal activation, proliferation, and/or lymphokine production of T lymphocytes, or subsets thereof.

BACKGROUND OF THE INVENTION

Most immune responses involve many components of the immune system. Although the immune mechanisms involved in the elimination of malignantly transformed cells are not well understood, it is reasonable to assume that if more immune mechanisms are activated and enhanced, the tumorous cells may be eliminated more effectively. Also, both humoral and cellular mechanisms are known to be involved in the immune response against viruses and virus-infected cells. Thus, generally speaking, for treatment of patients with various cancers or infectious diseases, and for protecting individuals exposed to infectious agents from contracting the infection, it is desirable to enhance the entire immune system.

The various branches of the immune system include antibodies, cytotoxic T cells (CTLs), T cells mediating delayed-type hypersensitivities ($T_{TDH}$ cells), monocytes and macrophages, natural killer (NK) cells, K cells mediating ADCC, and granulocytes. Complex interactions are involved in the activation of these various branches. The helper T cells ($T_h$ cells) play central regulatory roles, and many factors are secreted by these cells and other cells in a certain concerted fashion during the activation and proliferation phases. There is good reason to believe that the concerted production of lymphokines and cytokines, at the appropriate time and in the proper relative proportions, is important for maximizing the immune response.

Potentiation of the immune system is desirable for treating a number of pathological conditions, e.g., for treatment of malignant tumors, such as those associated with renal cell carcinoma and malignant melanoma. The immune potentiators include substances identified from screening natural sources, such as cultures of microorganisms, marine animals, herbs, or plants, as well as substances screened from large batteries of synthetic organic compounds.

One example of a substance from a natural source is muramyl dipeptide, which has been identified as the smallest structure from the cell wall of staphylococcal bacteria which still retains immune potentiating effects. Many analogues of muramyl dipeptide have been synthesized. Muramyl dipeptide and its analogues are macrophage activators, and have been tested and developed as therapeutic agents for tumors and as adjuvants for vaccines.

Other examples of immune potentiators derived from natural sources include double-stranded RNA and mismatched double-stranded RNA (also called ampligen) which can induce interferon synthesis and other immune functions. These substances have also been tested for treating tumors and viral diseases, such as AIDS.

Immune potentiators may be applied to patients alone or in combination with surgery, irradiation, or chemotherapy. They may also be desirable for treating patients with viral infectious diseases or for protecting individuals, after exposure to viruses, from contracting infection. Immune potentiators may be useful as adjuvants for various vaccines for infectious diseases or cancers.

Recently, recombinant human lymphokines and cytokines have been produced by genetic engineering. Many such recombinant "biological response modifiers" are being tested for treatment of various cancers and infectious diseases. A few recombinant products, such as interleukin-2 (IL-2), α-interferon, γ-interferon, granulocyte-colony stimulation factor and granulocyte/monocyte-colony stimulation factor (G-CSF, GM-CSF), have been approved in many countries for use against certain cancers and infectious diseases. For example, IL-2 is approved for treating patients with renal cell carcinoma; α-interferon is approved for treating patients with hairy cell carcinoma or with hepatitis B infection; G-CSF and GM-CSF are approved for treating cancer patients receiving chemotherapy for the purposes of restoring lost neutrophils.

Individual recombinant lymphokines, such as IL-2, IL-4, or γ-interferon can augment some aspects of the immune system, but function only against limited immunocyte targets and can only potentiate certain immune functions and not the entire immune system. They also probably function only over short ranges and in limited areas in vivo. Also, cytokines and lymphokines which are injected into patients are cleared rapidly through the kidneys. They likely will not be present in sufficiently high concentrations in the lymphoid system for long enough to achieve their desired immunological effects.

Of the various substances other than lymphokines or cytokines which have been studied for potentiating the immune system, most which are suitable for in vivo use do not target or enhance the T cells directly. For example, muramyl dipeptide, and analogues thereof, primarily activate macrophages. Double-stranded RNA and mismatched double-stranded RNA mainly induce interferon production by a variety of cells.

A few naturally-derived protein substances are known to be potent T cell mitogens in culture in vitro, and have been used in studies to characterize and quantitate T cell activity. These substances include phytohemagglutinin A (PHA), concanavalin A (Con A), wheat germ agglutinin (WGA), and some other lectins, defined as carbohydrate-binding plant proteins. However, these T-cell mitogenic proteins, although very useful for in vitro studies, have poor specificity and therefore bind to almost all cell types. Because they are toxic and lack specificity, they are not effective for in vivo use as T cell potentiators.

In order to activate and expand lymphocytes to achieve satisfactory therapeutic effects while avoiding administering toxic substances, some groups have sought to activate and expand the T lymphocytes from patients in culture in vitro for a period of time under optimal conditions and then harvest the activated cells and inject them back into the same patients. In this so-called IL-2/LAK therapeutic regimen, used by the Biological Therapy Institute (Franklin, Tenn.) to treat patients with various cancers, the blood is first drawn from the patients and the mononuclear cells are isolated. See Rosenberg, S. A. et al., *N. Eng. J. Med.* 316:889 (1987). The cells are incubated in medium containing recombinant IL-2 for several weeks, and the activated and expanded T cells, which contain the lymphokine-activated killer (LAK) cells, are harvested and injected into the patients.

A more recent, modified version of this IL-2/LAK therapy, known as autolymphocyte therapy (ALT) has been developed by Cellcor Therapies, Inc. in Boston Mass. See Osband, M. E. et al., *Lancet* 335:994 (1990). The lymphocytes from renal cell carcinoma patients are taken twice. The first time, the lymphocytes are stimulated with antibodies specific for human CD3 antigen (anti-CD3) in vitro to produce lymphokines. The culture supernatant is collected after a few days of culturing, and the cells are discarded. The second time, the lymphocytes taken from the patients are incubated in the autologous lymphokines for a period of five days and the cells are harvested and injected into the same patients.

It is claimed that these approaches, involving in vitro lymphocyte stimulation and expansion, achieve beneficial responses in a portion of the treated patients. The major concern with these regimes is that the treatment is very tedious, expensive, and requires sophisticated, specialized cell culture facility. The variation among cells or cultures from different patients requires demanding monitoring procedures. Also, lymphocyte cultures have very poor viability even under optimal conditions, meaning that during the culturing, large numbers of the cells will die. When large numbers of dead cells are injected into patients, this may actually burden the reticuloendothelial system (RES) and reduce its effectiveness in combating the tumor cells.

In summary, the clinical studies and approved routine uses of IL-2 and γ-interferon and of LAK or ALT therapies indicate that T cell activation and expansion can achieve therapeutic effects in some patients with cancers or infectious diseases. On the other hand, the results of these treatments suggest that the lymphokine treatments have certain deficiencies and the LAK and ALT treatments have some substantial drawbacks. Thus, an efficacious and feasible treatment may be realized if these deficiencies can be eliminated.

A number of MAbs specific for CD3 on the surface of human T cells (pan T marker) are known to be very potent mitogens of human T cells in vitro, e.g., the MAb OKT3. Van Wauwe, J. P. et al., *J. Immunology* 124:2708 (1980); Chang, T. W. et al., *Proc. Natl. Acad. Sci. U.S.A.* 78:1805 (1981); MAb 64.1 Hansen, J. A. et al., *Leukocyte Typing: Human Leukocyte Differentiation Antigens Detected by Monoclonal Antibodies*, Eds. Bernard, A. et al. (Spring Verlag, New York, 1984). In medium containing only fetal calf serum and no human serum (and therefore no IgG), the anti-CD3 MAbs are much more potent than PHA or Con A in inducing T cell proliferation.

But the mitogenic effect of anti-CD3 requires both specific binding to the CD3 antigen and the presence of the Fc moiety of the antibody, as well as the presence of monocytes and macrophages. The best explanation for these results is that the Fc of the anti-CD3 MAbs binds to the Fc receptors on monocytes/macrophages, thereby aggregating the CD3 antigen on the T cell surface. Since CD3 is associated with the T cell antigen receptors, the aggregation of CD3 triggers the activation and proliferation of the T cells.

This explanation is supported by experiments which show that when the anti-human CD3 MAb is conjugated to Sepharose 4B beads or coated on the substratum plastic surface of culture wells, monocytes and macrophages are not needed to induce activation and proliferation of T cells. See Williams, J. M. et al., *J. Immunol.* 135:2249 (1985); Ceuppens, J. L. & Baroja, M. L., *J. Immunol.* 137:1816 (1986); Geppert, T. D. & Lipsky P. E., *J. Immunol.* 138:1660 (1987). Based on these experiments, it has been suggested that the solid-phase anti-CD3 MAb functions by aggregating the CD3 antigen on the T cell surface.

However, when anti-human CD3 is injected in vivo, the results are the opposite of the in vitro effects. OKT3 MAb, which is the first MAb ever approved for therapeutic use in vivo, is strongly immunosuppressive and is approved for use as an immunosuppressor for patients receiving kidney transplants. Ortho Multicenter Group Study, *N. Eng. J. Med.* 313:337 (1985). The injection of OKT3 causes rapid depletion of T cells from the circulation. Although the mechanism by which anti-CD3 causes this rapid depletion of T cells is not well understood, the best explanation is that anti-CD3 induces ADCC of the T cells, i.e., as the T cells coated by anti-CD3 circulate through the spleen and liver, they are lysed by the phagocytic cells of the RES in these organs. It is also possible that some of the T cells are destroyed by complement-mediated cytolysis and some other cytolytic mechanisms.

In in vivo mouse studies using a hamster MAb against murine CD3, it has been shown that low doses of anti-CD3 can prevent malignant progressive tumor growth and protect against lethal sendei virus infection. Ellenhorn, J. D. et al., *Science* 242:569 (1988); Kast, W. M. et al., *J. Immunol.* 145:2254 (1990). It has been suggested that the T cells in the mice are activated by such treatment with anti-CD3. Hirsch, R. et al., *J. Immunol.* 142:737 (1989).

Human and murine studies involving in vivo administration of anti-CD3 indicate that there is a substantial difference between the two species. In humans, even minute amounts of anti-CD3 are immunosuppressive and cytolytic. Also, the activation and mitogenic effect of anti-CD3 on T cells is completely blocked by the presence of human serum or IgG. Chang, T. W. et al., *Proc. Natl. Acad. Sci. U.S.A.* 78:1805 (1981); Looney, R. F. and Abraham, G. N. *J. Immunol.* 133:154 (1984). These results suggest that whole anti-CD3, or fragments thereof, will not activate T cells in vivo, and therefore, the invention described below is not suggested.

SUMMARY OF THE INVENTION

The immunoregulatory substances of the invention include: a mixture of F(ab')$_2$ fragments (or other divalent binding molecules which lack Fc) which each bind noncompetitively to different monovalent antigenic epitopes on the same antigen; the F(ab')$_2$ fragment (or other divalent binding molecules which lack Fc) of a bispecific antibody which has each of its binding sites derived from one of the two MAbs that bind noncompetitively (i.e., without significant hindrance from each other) to monovalent antigenic epitopes on the same antigen; a conjugate including a polymeric backbone, such as polyethylene glycol ("PEG"), cellulose, dextran, agarose, an amino acid copolymer, a liposome, or microbeads that is coupled with binding molecules, e.g., Fv, Fab, F(ab')$_2$, or a whole antibody which binds noncompetitively to monovalent antigenic epitopes on the same antigen; a conjugate including a polymeric backbone that is coupled with binding molecules, e.g., Fv, Fab, F(ab')$_2$, or a whole antibody, wherein one of the binding molecules specifically targets the CD3 antigen on T cells and wherein the other binding molecule(s) specifically targets one or more of the other antigen(s) on T cells, such as CD2, CD4, CD5, and CD8.

The immunoregulatory substances of the invention are specific for a surface antigen of T cells or subsets thereof. These antigens include: CD3, idiotype bearing receptor chains and other T cell receptor (TCR)-linked components; CD4, CD8, and other T cell-specific surface components. Many of these antigens contain only a single binding site for each MAb (i.e., a monovalent antigenic epitope).

The main use for the immunoregulatory substances is as immune potentiators, which activate and expand T cells or a subset of the T cells, and stimulate them to produce IL-2, γ-interferon, IL-1, IL-4, IL-6, tumor necrosis factor (TNF), or other lymphokines. Because T cells play central roles in the regulation of many branches of the immune system, the concerted secretion of a number of lymphokines will activate many immune mechanisms, whereas the administration of individual lymphokines will have a more limited effect.

Such immune potentiators may be used to treat patients with cancers or infectious diseases, or to protect individuals exposed to infectious agents from contracting the infections. The immune potentiators might be particularly well suited for treating renal cell carcinoma, malignant melanoma, colon carcinoma, and small cell lung carcinoma. Infectious diseases appropriate for treatment with immune potentiators include hepatitis, and particularly hepatitis B and C, herpes simplex I and II, condyloma, influenza, and pneumonia. Immune potentiators may also be used as adjuvants for vaccines, which could reduce the number of times that a vaccine needs to be administered in order to be effective in prophylaxis. This could be particularly effective for vaccination against diphtheria, influenza, and measles, as there already are mass vaccination programs for children against these diseases.

The immune potentiators could also be used in veterinary practice, particularly to treat companion animals affected with cancers or chronic infections. For use in veterinary practice, the same substances of the invention mentioned above are employed, with the fragments and antibodies targeting the T cell antigen of the animal one is seeking to treat. Among the diseases in companion animals which might be particularly well suited for treatment with the products of the invention are the canine distemper adenovirus, coronavirus, or Rabies virus, and the feline leukemia virus. Embodiments of the invention suitable for treating feline leukemia virus include antibodies and fragments which target feline CD3, which are coupled with microbeads or other polymer backbones.

Many of the antigens on T cells (or subsets thereof) contain only one antigenic epitope which is specific for one unique MAb. The one MAb fragment by itself cannot cross-link and aggregate the surface antigen, which is often required for cell activation. In contrast, the products of this invention are designed to cross-link and aggregate the surface antigens without triggering complement-mediated cytolysis or antibody-mediated cellular cytotoxicity (ADCC) in vivo.

In one embodiment, the invention includes $F(ab')_2$ fragments (and other divalent binding molecules lacking Fc) which accomplish these objectives. The first fragments of the invention (including $F(ab')_2$ and other divalent binding molecules) bind noncompetitively to monovalent antigenic epitopes on the same antigen. The second fragments of the invention (including $F(ab')_2$ and other fragments) are derived from a bispecific antibody which has each of its binding sites derived from one of the two MAbs that bind noncompetitively to monovalent antigenic epitopes on the same antigen.

In another embodiment, the invention includes a molecular backbone or base or microbead to which binding molecules (including Fv, Fab, $F(ab')_2$, or whole antibodies) may be conjugated. The backbone or microbead may be PEG, cellulose, dextran, agarose or other hydrophilic polymers. Active groups for cross-linking may be introduced by established methods. Alternatively, long chain peptides containing Lys, or Cys residues may be synthesized. A preferred family of amino acid copolymers are synthesized by a routine method, containing Gly, Ser, and Lys (or Cys) at 20:4:1 ratio, with molecular weights of 10,000 to 1,000,000 (about 150 to 15,000 amino acid residues long). Liposomes may also be used as the base for conjugating with the antibodies and fragments.

DETAILED DESCRIPTION OF MAKING AND USING THE INVENTION

As noted above, the immunoregulatory substances of the invention include: a mixture of $F(ab')_2$ fragments (or other divalent binding molecules which lack Fc) which each bind noncompetitively to different monovalent antigenic epitopes on the same antigen; the $F(ab')_2$ fragment (or other fragments which lack Fc) of a bispecific antibody which has each of its binding sites derived from one of the two MAbs that bind noncompetitively to monovalent antigenic epitopes on the same antigen; a conjugate including a polymeric backbone, such as polyethylene glycol ("PEG"), cellulose, dextran, agarose, or an amino acid copolymer, a microbead or a liposome, that is coupled with binding molecules, e.g., Fv, Fab, $F(ab')_2$, or whole antibodies, which bind noncompetitively to monovalent antigenic epitopes on the same antigen.

The Fv fragments of the MAbs may be produced in bacteria using single chain antibody technology, as described in U.S. Pat. No. 4,946,778 and International Application No. WO88/09344. The Fv may also be genetically engineered to contain glycosylation sites and produced in mammalian cells, to result in a fragment containing carbohydrate moieties.

The Fab or $F(ab')_2$ may be produced by enzymatic cleavage of whole IgG which is produced by a hybridoma or a transfected cell lines (a myeloma or a cell line such as Chinese Hamster Ovary (CHO)), using pepsin and papain digestion, respectively.

The Fab or $F(ab')_2$ fragments, or the whole antibodies, may be wholly animal or human derived, or they may be in chimeric form, such that the constant domains are derived from the constant regions of human immunoglobulins and the variable regions are derived from the parent murine MAb. Alternatively, the Fv, Fab, or $F(ab')_2$ may be humanized, so that only the complementarity determining regions (CDR) are derived from an animal MAb, and the constant domains and the framework regions of the variable regions are of human origin. See, e.g., U.S. patent application Ser. No. 07/952,802, filed Sep. 25, 1992, for a detailed example of how to make a particular type of humanized antibody. These chimeric and humanized antibodies and fragments are less immunogenic than their wholly animal counterparts, and thus more suitable for in vivo use, especially where administration will be over prolonged periods.

Methods of making chimeric and humanized antibodies are well known in the art, (see, e.g., U.S. Pat. No. 4,816,567, International Application No. WO84/03712, respectively). The Fv, Fab, or $F(ab')_2$ fragments may be produced from such chimeric or humanized antibodies using proteolytic digestion, as described above.

The antibody fragments can be conjugated to the linear or cross-linked backbone, microbead or liposome using conventional techniques, well known in the art. See, e.g., Ostro, M. J. (Ed.), *Liposomes: from Biophysics to Therapeutics* (Marcel Dekker, New York, 1987). One preferred method of preparing liposomes and conjugating immunoglobulins to their surface is described by Ishimoto, Y. et al., *J. Immunol. Met.* 75, 351–360 (1984). Multilamillar liposomes composed of dipalmitoylphosphatidylcholine, cholesterol and phosphotidylethanolamine are prepared. Purified fragments can then be coupled to the phosphatidylethanolamine by the cross-linking agent N-hydroxysuccinimidyl 3-(2-pyridyldithio) propionate. The coupling of the antibody or fragment to the liposome can be demonstrated by the release of a pre-trapped marker, e.g., carboxyfluorescence, from the liposomes upon the treatment of secondary antibody against the conjugated antibody, fragment and complement.

The antibodies or fragments may also be coupled to a liposome or another carrier of the invention via their carbohydrate moieties. Provided that the carbohydrate moiety is not in the hypervariable region or at the antibody binding sites, the conjugation via the cross-linking with the carbohydrate will not affect binding, as the binding sites will still be available to bind to cell surface antigens.

One preferred way to couple antibodies and fragments of the invention (other than Fv) to a polymer backbone or a liposome is to conjugate them through the carbohydrate moiety on the constant regions. This will maximize the binding sites which are available, and not hindered, for binding to the antigens.

Methods for derivatizing sugar ring moieties to create hydrazide groups for coupling with fragments (and antibodies) has been established. See Rodwell, J. D. et al., *Proc. Nat'l Acad. Sci. USA* 83:2632–36 (1986). Several immunoconjugates prepared in this way are in clinical studies or pending approval for routine clinical uses.

The polymers for conjugating to the antigen binding sites can be modified to generate active groups for coupling according to established methods. For example, PEG can be derivatized by 1,1'-carbonyldiamidazole to form imidazole carbamate active groups, which react with amino groups of proteins. Beauchamp, C. O. et al., *Anal. Biochem.* 131:25 (1983). Similar reactions can be used for derivatizing agarose. Bethell, G. S. et al., *J. Biol. Chem.* 254:2572 (1979).

The antibodies or fragments can be coupled directly to the derivatized, activated polymers. Bifunctional cross-linkers suitable for conjugating the activated polymers (or liposomes) and the antibodies or fragments, can be selected based on the properties desired and the specific substances to be cross-linked. These heterobifunctional reagents are available from several commercial sources, e.g., Pierce Chemical Co., Rockford, Ill., and the reaction procedures are well-known.

The substances of the invention, in appropriate pharmaceutical vehicles, may be administered intravenously (i.v.), so that they can reach spleen, liver, and various lymph nodes. They will also reach the T and B cells in circulation when administered i.v.

The substances of the invention may also be given intraperitoneally (i.p.), where they will mainly interact with cells in the peritoneal cavity and will be delivered to other lymphoid tissues through the lymphoid circulation. The T cells which are activated and expanded in the spleen and peritoneal cavity may also travel to different tissues in the circulation.

The substances of the invention may also be injected directly into or near the solid tumors, warts, or other affected tissues. In this case, the T cells will be activated and expanded and mediate various immune mechanisms.

Certain substances of the invention may only induce the activation of resting lymphocytes and not their proliferation. In such case, their administration may be followed by T or B cell growth factors, such as IL-2, or IL-4.

The substances of the invention may be given alone, or in combination with surgery, irradiation treatment, or chemotherapy for cancer patients, or in combination with viral antibiotics or other anti-viral substances for patients with infectious diseases.

There is adequate experimental support for the efficacy of the invention. As noted above, the interaction between the Fc of the anti-CD3 MAbs and the Fc receptors (FcR) on monocytes/macrophages is required both for the mitogenic effect in vitro and the ADCC effect in vivo. It was first found that the $F(ab')_2$ and Fab fragments of OKT3, which lacked Fc, were no longer mitogenic and also that whole OKT3 could not induce the T cells to proliferate if the monocytes were depleted from the mononuclear cells in culture. Van Wauwe, J. P., et al., *J. Immunol.* 124:2708 (1980); Chang, T. W., et al., *Proc. Natl. Acad. Sci. U.S.A.* 78:1805 (1981). It was then suggested that the mechanism of anti-CD3 mitogenic effect involved the interaction between the Fc of anti-CD3 and FcR on monocytes, because human serum, purified human IgG, or isolated Fc fragments could block the mitogenic effect of OKT3. Looney, R. F. and Abraham, G. N., *J. Immunol* 133:154 (1984); Chang, T. W., *Immunol. Today* (1985). Several studies also showed that the deficiency of FcR for IgG on monocytes would impair the mitogenic effects of anti-CD3, supporting the notion that Fc-FcR interaction is important for the mitogenic effects of anti-CD3. Ceuppens, J. L., et al., *J. Immunol.* 135:3882 (1982); Tax, W. J. M., et al., *Nature* 304:445 (1983); Tax, W. J. M., *J. Immunol.* 133:1185 (1984).

A few studies examined the mitogenic mechanism of anti-CD3 further. It was found that anti-human CD3 MAb densely conjugated to sepharose 4B beads and purified human IL-1 could induce the proliferation of T cells in culture in which the antigen presenting monocytes were completely depleted. It was concluded that the anti-human CD3 MAb-Sepharose 4B could activate the resting human T cells and the IL-1 was then able to initiate the synthesis of RNA, IL-2 secretion, IL-2 receptor expression, and ultimately, DNA synthesis. Williams, J. M., et al., *J. Immunol.* 135:2249 (1985). It was also reported that in the complete absence of monocytes, the T cells could be induced to proliferate by incubation in plastic culture plates coated with anti-human CD3 MAb, if soluble anti-human CD5 MAb was also provided in the culture medium. Ceuppens, J. L. and Baroja, M. L., *J. Immunol.* 137:1816 (1986). Later it was reported that the resting T cells depleted of accessory monocytes could proliferate in wells of microtiter plates coated with high concentration of anti-human CD3 (for 64.1 MAb, 40–1000 ng/ml) without the addition of IL-2 or monocytes. Geppert, T. D. and Lipsky, P. K., *J. Immunol.* 138:1660 (1987).

Anti-CD3 MAb in an appropriate pharmaceutical composition, such as in soluble or suspension form, may also be mitogenic instead of being immunosuppressive in vivo. However, solid plastic sheets or large Sepharose 4B beads, although suitable for in vitro use, may not be appropriate for in vivo use. These solid materials, whether administered i.p. or by other routes, will be maintained in situ. They cannot be transported throughout the lymphoid system by the lymphoid circulation. For in vivo use, hydrophilic, soluble polymers, microbeads, or liposomes suitable for conjugating with large numbers of anti-CD3 MAb are preferred.

When anti-CD3 MAb molecules are conjugated to the polymer backbones, microbeads or liposomes, the Fc portion of anti-CD3 MAb will be accessible to monocytes and macrophages and other cells of the RES, and hence will facilitate phagocytosis and clearance of such conjugates. To minimize such clearance and to ensure that the mitogenic effect of anti-CD3 will be the dominant effect, and that any suppressive effect mediated by ADCC and complement-mediated cytolysis will be the lessened to low levels, fragments of anti-CD3 MAbs which are devoid of the Fc domains (i.e. Fv, Fab, and F(ab')$_2$) and which do not cause the Fc-dependent ADCC and complement-mediated cytolysis, are conjugated to the polymer backbones, microbeads or liposomes. The experiments with solid-phase bound anti-CD3 MAbs suggest that under certain conditions, the Fc domain of the antibody is not required in mitogenesis.

Among the surface molecules that are involved in the regulation of the activities of lymphocytes, the most important are the components or molecules associated with the TCR on T cells and mIg on B cells. These antigen receptors interact with antigens or antigen-presenting cells, and respond to antigen stimulation by causing the cell to undergo a sequence of activation, clonal expansion, and differentiation. The activation and expansion of lymphocytes consequently leads to various immune reactions and responses.

The TCR complex is very complicated and the structure is not fully characterized, despite extensive study. The information available indicates that the "complete" TCR complex contains one $\alpha$ chain, one $\beta$ chain, one $\gamma$ chain, one $\epsilon$ chain, one $\zeta$ chain, and a homodimer $\delta$ chain. The $\alpha$ and $\beta$ chains are clonally different and the $\alpha/\beta$ dimer is customarily referred to as the TCR. The remaining components of the TCR complex ($\gamma$, $\epsilon$, $\zeta$, and $\delta$ chains) are not polymorphic and are categorically referred to as the CD3 antigen.

It is known that T cells at different differentiation stages or with different functions express different sets of the chains. See e.g., Baniyash, M. et al., *J. Immunol.* 263:9874 (1988); Geisler, C. et al., *J. Immunol.* 145:1761 (1990). Thus, within the TCR complex on most T cells, the antigenic epitopes recognized by most MAbs are monovalent (one single epitope per complex).

It is possible that since there are two $\delta$ chains in the TCR complexes of some T cells, there may be two antigenic sites for some MAbs recognizing the CD3-$\delta$ chain. Among these MAbs, some may be able to cross-link the CD3/TCR complexes. Because the $\delta$ chain is relatively small (16 Kd), only a small portion of it is exposed to the exterior surface. Some MAbs specific for the CD3-$\delta$ dimer may bind to one of the two divalent antigenic epitopes which are physically close together and preclude the binding of another anti-CD3-$\delta$ MAb at the same site. Thus, for practical purposes, this latter group of MAbs (which is likely a small group), although they also bind to divalent antigenic sites, they cannot cross-link the CD3/TCR complexes.

It has been suggested that in the mitogenesis of T cells with anti-CD3, the monocytes, through the interaction between Fc of anti-CD3 and the FcR on monocytes, can aggregate the CD3 antigen on the surface of T cells. Since CD3 is associated with the TCR, the aggregation of the TCR complexes triggers the activation and subsequent proliferation of the T cells. Some MAbs specific for the CD3-$\delta$ chain may recognize a divalent antigenic epitope and can cross-link and aggregate the CD3/TCR complexes. Most anti-CD3 MAbs are likely specific for a monovalent antigenic epitope on CD3-$\gamma$, CD3-$\epsilon$, or CD3-$\zeta$, or even on CD3-$\delta$. Thus, anti-CD3 MAb in soluble form cannot trigger activation and proliferation of T cells because the antigenic epitopes on the CD3 molecules which are recognized by anti-CD3 MAb are likely monovalent. Accordingly, the MAb or F(ab')$_2$ can bridge the surface molecules and form multiple pairs of CD3, but cannot cross-link and aggregate them. Thus, by using two or more anti-CD3 MAbs, each binding to a monovalent antigenic epitope on CD3 in a noncompetitive fashion, the CD3 antigen may be cross-linked and aggregated, and thereby, the T cells will be triggered to activate and proliferate. To avoid the cytotoxicity caused by the Fc domain of the anti-CD3 MAb, F(ab')$_2$ derived from whole IgG, or genetically engineering F(ab')$_2$, are preferred.

To cause cross-linking and aggregation without the help of monocytes, two or more MAb fragments, each recognizing a monovalent antigenic epitope, are required. It can be appreciated that if three different anti-antigen MAbs are used, the cross-linking and aggregation will be even more pronounced.

A bispecific F(ab')$_2$ with two specificities, respectively being for the two monovalent antigenic epitopes of CD3, can cross-link and aggregate molecules, although some singly-paired molecules will be left on the T cell surface. These F(ab')$_2$ preparations will therefore also induce T cell activation and proliferation.

Another means to achieve cross-linking of antigenic epitopes on T or B cell surfaces is to use plastic sheets or microbeads coated or conjugated with anti-CD3 MAbs. These may be implanted or deposited or administered i.v. into certain body sites in order to trigger mitogenesis. Thus, the appropriate backbone or base upon which to conjugate anti-CD3 MAb should be polymers which are hydrophilic, stable, non-immunogenic, nontoxic and resistant to hydrolases (e.g. glycosidases and proteases) in the serum and other body fluids in patients. Examples are PEG, cellulose, dextran, latex beads which are glutaraldehyde modified, and agarose, which each have different molecular sizes and are all well-characterized and studied.

Another suitable "backbone" is an amino acid copolymer. Preferred amino acid copolymers include Gly and Ser residues, and Lys, Cys, or other appropriate residues, for providing conjugation sites. Considering the molecular sizes of Fv, Fab, F(ab')$_2$, and whole antibodies, the optimal spacing between the adjacent Lys or Cys residues is in the range of 15 to 25 amino acids. Thus, a preferred amino acid copolymer has a composition of $(Gly_{15}Ser_5Lys)_n$, where n is 5 to 600.

The fragments or antibodies of the invention can also be conjugated to liposomes, using the methods described above, wherein reactive groups for cross-linking are introduced on the surface of the liposomes and the fragments are coupled thereto. For certain clinical applications with certain MAbs, fragments (or binding molecules) conjugated to liposomes may be more preferred than fragment/polymer conjugates, as the liposome conjugates can interact with antigen on T cells by a mechanism more closely resembling the interaction between cells, than when the fragment is presented on a polymer backbone.

The mitogenicity of the polymerized binding molecules of the invention probably depends on their sizes; more specifically, on the number of binding sites per molecular conjugate. The preferred molecular conjugates are those which are small but still are able to induce optimal mitogenic effects. Many suitable polymers are available commercially in different lengths or sizes. Amino acid copolymers of different lengths can also be synthesized and fractionated by molecular sieve chromatography. Polymers such as cellulose or agarose can be treated with specific enzymes, e.g., cellulase and agarase, to yield different lengths.

Good cross-linking and aggregation can also be obtained with other embodiments. For example, a polymer backbone can be coupled with a number of monovalent Fab fragment against an antigenic epitope of a T cell. This embodiment functions similarly in principle to the other embodiments, the difference being that there are more binding sites in such molecular conjugates than in the F(ab')$_2$. Because of the larger numbers of binding sites, the cross-linking and aggregation will be more complete and there will be fewer singly-paired molecules, which are not cross-linked.

As noted above, the invention is not limited to anti-CD3 fragments, but also includes binding molecules, fragments (and conjugates thereof) which are specific for surface antigens of human T lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products result even though the in vivo effects of IgG specific for T cells are primarily cytolytic effects mediated by complement, ADCC, or other cytolytic mechanisms. In addition to anti-CD3, other examples of antibodies which initiate these cytolytic effects in vivo are anti-CD4, Alters, S. E., et al., *J. Immunol.* 144:4587 (1990), and other antibodies against the T cell receptor. All of these antibodies are known to cause target cell depletion in vivo. However, like anti-CD3, when formulated according to the invention, they would activate or modulate their respective target cells in vivo. Similarly, one would expect that MAbs specific for components associated with the mIg on B cells would also activate or modulate the target cells.

It is noted that, unlike the fragments of the invention which are mixtures of fragments binding to at least two different antigenic determinants, single MAbs which bind to monovalent antigenic determinants cannot cross-link the antigens on the cell surface. In order to stimulate cell activation and proliferation, cross-linking of the surface antigens is usually required. However, many surface molecules such as CD4 or CD8 are single polypeptide chains or are composed of different polypeptide chains, and cannot be efficiently cross-linked by a single divalent antibody recognizing monovalent antigenic epitopes.

Further, some surface antigens contain two identical polypeptide chains, e.g., surface immunoglobulins on B cells contain 2 H chains and 2 L chains. There are not always two or more antigenic determinants on these surface antigens. If the antigenic site is on the Fab domain, there will be two antigenic sites for the MAb. However, if the antigenic site is on the Fc, there may be one or two antigenic sites which can be bound by a MAb. When the antigenic epitope recognized by a MAb is conformationally formed by two H chains, for practical purposes there is only one antigenic site, because the two sites are physically so close that only one MAb molecule can bind to them. The binding of one MAb molecule to one site precludes the binding of a second MAb molecule to the other site. Therefore, for many surface antigens, although polyclonal antibodies which recognize many different epitopes can almost always cross-link, MAbs may link two molecules but often may not cross-link and aggregate them. The conjugates of the invention, which recognize monovalent antigenic epitopes, may achieve the same cross-linking effects as polyclonal antibodies.

The fragments of the invention, which are likely to have certain immunoregulatory effects in polymerized forms in vivo, include those which are specific for CD4, CD8, and components of TCR complexes. Specific examples are fragments of the monoclonal antibody OKT3, which targets the CD3 antigen on T cells. Fragments binding to a surface antigen which is expressed by only T cells, or a subset of them, are potentially useful as in vivo immunomodulators in polymerized forms.

EXAMPLE 1

Developing Murine Monoclonal Antibodies Against CD3 Antigen of a Non-Human Animal A method of making monoclonal antibodies specific for the CD3 antigen of any mammal (including companion animals, such as dogs, cats, and horses, agricultural animals, such as cattle, and others) can be readily formulated from what is known about human and murine CD3 antigen and about the properties of antibodies specific for these antigens. The procedure is similar to those described for the making of anti-human CD3 monoclonal antibodies, by Kung, P. C. et al Science 206:347–349 (1979) and by Leo, O. et al Proc. Natl. Acad. Sci. U.S.A. 84:1374–1378 (1987).

The molecular weight and the subunit composition of the CD3 antigen is known for humans and mice, and is expected to be almost identical among different animal species. The human and murine sequences of CD3 subunit polypeptides are also known.

For immunizing mice against the CD3 antigen, fresh thymus tissue is obtained from the animal against which murine anti-CD3 monoclonal antibodies are to be prepared. Single cell suspensions are prepared by mincing the thymus tissue. The single cells are used for immunizing mice, at dosage of $1 \times 10^7$ thymocytes per intraperitoneal injection per mouse, for a total of three injections at two week intervals between injections. Four days after the last injection, the mice are sacrificed and their spleens are removed for fusion with NS0 or SP/20 cells, following the standard procedure for making hybridomas. The supernatants of the growing hybrids from the primary fusion wells in the microculture plates are screened for binding to the single thymocytes using immunofluorescence flow cytometry. The fluorescent probe for the immunofluorescent staining is FITC-labelled rat monoclonal antibody against murine IgG2a and IgG2b. Alternatively, the antibodies may be biotin-conjugated and used in combination with FITC-labelled avidin.

The fusion wells showing binding to the thymocytes are then cloned by limiting dilution, and the subclones are tested again for binding to the thymocytes using the immunofluoresence flow cytometry. The positive clones are further tested for mitogenic effects on T cells. For this test, peripheral blood is obtained by venipuncture. The mononuclear fraction, which contains lymphocytes and monocytes, is prepared by centrifugation on a Ficoll-Hypaque cushion, with the same procedure applied to human and murine mononuclear cells. A proliferative response assay employing $^3$H-thymidine incorporation technique is used to determine the cellular proliferation. The clones with supernatants which are highly mitogenic on the mononuclear cells are then isolated for further characterization.

The specific reactivity of the monoclonal antibodies with the CD3 antigen can then be confirmed by, for example, the immunoprecipitation and Western blotting procedures. In the immunoprecipitation method, the thymocytes are surface-labelled with $^{125}$I with a lactoperoxidase procedure. Lysates of the labelled cells are prepared with NP40 detergent. The antigens reactive with the antibodies in question are bound and precipitated by the antibodies. The precipitates are then resolved by 1-D or 2-D SDS polyacrylamide electrophoresis (SDS PAGE). The pattern and the sizes of the bands are then compared with the CD3 antigen of human and murine origin, to confirm that the CD3 antigen, in fact, is bound.

In the Western immunoblotting method, the lysates of unlabelled thymocytes are run on SDS PAGE. The proteins are then electro-transferred onto a nitrocellulose paper, which is then incubated with the antibodies in question. After washing, the bound murine antibodies are localized with enzyme-conjugated goat IgG against murine IgG. The size of the reactive bands are compared to those of the human and murine CD3 antigen. For confirmation, the antigenic peptide can be isolated by 2-D SDS gel electrophoresis, and the N-terminal amino acid sequences can be determined and compared to those of human and murine CD3 antigen.

The appropriate antibodies can then be derivatized, and/or conjugated, as described above, in order to make products of the invention. These products can be used for T cell mitogenesis in non-human mammals.

EXAMPLE 2

Testing Anti-CD3 MAbs for Noncompetitive Binding to CD3 on T cells

Various anti-CD3 MAbs can be purchased from commercial firms offering immunochemical reagents, including Ortho Diagnostic Systems, Raritan, N. J.; Becton Dickenson Immunological Reagents, Mountain View, Calif.; Coulter Diagnostics, Hialeach, Fla.; Sigma Chemical Co., St. Louis, Mo.; Boehringer Mannheim, Indianapolis, Ind.; Olympus Corp., Lake Success, N.Y. All these MAbs were developed by different groups. These firms offer anti-CD3 MAb not only in purified, plain IgG, but also in fluorescein-conjugated forms.

Additional MAbs against human CD3 can be readily prepared by hybridoma methodology as described by Kung, P. C. et al., Science 206:347 (1979). Using this method, many laboratories have developed murine anti-human CD3 MAb. The same methods could be used to develop anti-CD3 MAb against the CD3 of virtually any mammal or companion animal. These techniques are well known in the art, and involve the standard techniques of immunization, fusion and screening used to make hybridomas and monoclonal antibodies.

For determining whether two MAbs (or fragments) specific for CD3 can bind to CD3-bearing T cells simultaneously, fluorescence flow cytometric analyses may be applied. For these analyses a T cell line, such as human CEM (ATCC CCL119 from the American Type Culture Collection), or peripheral blood mononuclear cells, can be used for the cell staining. The assay is to determine whether the binding of a FITC or rhodamine-labeled anti-CD3 MAb to the cells will be inhibited by the presence of varying concentrations of a second anti-CD3 MAb. The assay should also be reversed to determine whether the binding of the fluorescence-labeled second anti-CD3 is inhibited by the presence of the other anti-CD3.

If the binding of each anti-CD3 to the T cells is not significantly affected by 5–10 fold concentrations of the other anti-CD3, it can be concluded that both anti-CD3 MAb can bind non-competitively to CD3 molecules on T cells. Additional confirming assays would measure whether the binding to T cells by the two MAbs is additive.

EXAMPLE 3

Conjugates of the Invention as in vivo Immune Enhancers in an Animal Model System Conjugates of the invention were made by conjugating whole IgG molecules or F(ab')$_2$ fragments of the hamster monoclonal antibody 145-2C11, which is specific for murine CD3-$\epsilon$ chain, onto latex microbeads. The latex beads (of a uniform 2.5 $\mu$m diameter) were glutaraldehyde modified and were purchased from Interfacial Dynamics Corporation (Portland, Oreg.). These beads were already modified to contain activated groups for coupling with proteins. Suspensions of these beads could be made homogeneous and suitable for injection with gentle shaking. 5 $\mu$g of 145-2C11.IgG, or 3 $\mu$g of 145-2C11.F(ab')$_2$, were conjugated onto 1 mg of the activated latex beads.

The constructs of 145-2C11.IgG/latex beads (abbreviated as "X.IgG/beads") and 145-2C11.F(ab')$_2$/latex beads ("X.F(ab')$_2$/beads") were shown to be as effective as free 145-2C11 (abbreviated as "X.IgG") in inducing the proliferative response of mouse spleen cells in a 3-day in vitro assay. Unconjugated, plain beads and the fragment 145-2C11.F(ab')$_2$ (abbreviated as "X.F(ab')$_2$") did not have significant effects on the proliferative response.

Various amounts of X.IgG/beads and X.F(ab')$_2$/beads were injected via the tail vein into adult BALB/c mice and their effects on the general physiology and the immune system of these mice were compared with those of mice injected with soluble X.IgG, X.F(ab')$_2$, and plain beads. The 65 mice receiving one injection of 4 to 16 $\mu$g of soluble X.IgG experienced a transient increase in spleen size which was evident 72 hours after the injection (day 3). By day 5, the spleens of these mice had begun to lose weight. The mice appeared feeble and lethargic as early as day 1 and lost 30 to 40% of their body weight by day 10. Ten of these 65 mice died, all within 4 days of the injection. The numbers of cells in the spleens of these mice that could be released by mechanically disrupting the spleens' connective tissue increased by 20–30% by day 3 and decreased to 40 to 60% of the normal levels by day 7. To a large extent, the decrease in the total spleen cells could be attributed to the loss of T cells, which were measured with a fluorescence flow cytometric method using a fluorescein isocyanate-labeled anti-Thy-1.2 antibody. In a normal mouse, T cells account for 25–35% of spleen cells. In the mice treated with X.IgG, T cells accounted for about 10% of the spleen cells on day 7. The T cells in the spleens of the treated mice remained at these low levels until day 10, and thereafter, increased, but still did not reach normal levels, even by day 14.

The mice that received one injection of up to 25 $\mu$g of soluble X.F(ab')$_2$ did not show signs of adverse effects. Their physical appearance was normal and their body weight was normal. None died. The total numbers of cells and the proportions of T cells in their spleens were not changed. These observations were consistent with the in vitro results that X.F(ab')$_2$ could not induce T cell activation and proliferation. Similarly, the mice that received one injection of unconjugated, plain latex beads at amounts up to 5 mg did not show any signs of abnormality.

In contrast, whole IgG or F(ab')$_2$ of 145-2C11 conjugated to latex microbeads (X.IgG/beads and X.F(ab')$_2$/beads) had the same effects as free 145-2C11.IgG (X.IgG) on stimulating the splenic T cells in the first 3 days. However, the bead conjugates had drastically different effects on the spleen T cells after day 3 and on the well being of the mice, as early as day 1. The mice receiving one intravenous injection of X.IgG/beads or X.F(ab')$_2$/beads, at up to 16 µg X.IgG and 25 µg X.F(ab')$_2$, respectively, developed an activated and expanded immune system. The spleen enlargement, as measured by weight or by the number of cells recovered from minced spleens, was noticeable by day 3, continued to increase until day 5 or day 6, and, thereafter, the spleens returned gradually to normal size by around day 10. The proportion of T cells in the spleens increased from 25–35% to 30–50%. Among these T cells, the proportions of activated T cells, as identified by the expression of interleukin-2 receptors on the cell surface using anti-CD25 and flow cytometry, increased dramatically from 4–6% to 13–21% by day 3.

All of the 123 mice injected with X.IgG/beads or X.F(ab')$_2$/beads appeared normal. Their agility was normal. They did not lose body weight in the two weeks after injection. None of them died. Pathological examinations revealed enlarged spleens and lymph nodes and no other major abnormal symptoms.

Another set of experiments were also ran in which mice were injected intravenously with 50 µg of chimeric human/mouse IgE (hu ε, k/mu $V_H$, $V_L$) from SE44 cells, alone and together with, respectively, X.IgG, and X.IgG/beads. Mice were also injected intraperitoneally with the chimeric human/mouse IgE together with complete Freund's adjuvant. As controls, beads and X.IgG/beads were also injected intravenously. The murine IgG response was then measured after 14 days.

The mice receiving the X.IgG/beads and chimeric human/mouse IgE had a much stronger IgG antibody response to human IgE than the mice which received only chimeric human/mouse IgE. The response of the mice receiving X.IgG/beads and chimeric human/mouse IgE was comparable to that of the mice receiving chimeric human/mouse IgE and complete Freund's adjuvant. Mice receiving soluble X.IgG with chimeric human/mouse IgE did not make a detectable antibody response, nor did mice receiving only the X.IgG/beads or only the beads.

In summary, these studies indicate that T cells and the immune system can be stimulated without T cell depletion in vivo by properly modified anti-CD3 antibodies.

EXAMPLE 4

Additional Anti-T Cell Immune Enhancing Products

As noted above, the invention is not limited to anti-CD3 antibodies and fragments, but also includes binding molecules, fragments (and conjugates thereof) which are specific for surface antigens of human T lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products, that are prepared according to the present invention, will result even though the in vivo effects of IgG specific for T cells are primarily cytolytic effects mediated by complement, ADCC, or other cytolytic mechanisms. In addition to anti-CD3, other examples of antibodies which initiate these cytolytic effects in vivo are anti-CD4 antibodies, Alters, S. E., et al., *J. Immunol.* 144:4587 (1990). All of these antibodies cause T cell depletion in vivo.

Anti-CD4 has been found to have stimulatory effects in vitro. This indicates that, like anti-CD3, when formulated into conjugates of the invention, they would activate or modulate their respective target cells in vivo. A number of studies have indicated that the activation of T cells with an anti-CD3 MAb can be enhanced by an MAb which is specific for a different surface antigen on T cells. These auxiliary MAbs include those specific for HLA class-1 antigens, HLA class-II antigens (such as Ia), CD2, CD4, CD5, CD8, CD28, or CD37. Ceuppens, J. L. et al., *J. Immunol.* 137:1816 (1986); Tutt, A. et al., *J. Immunol.* 147:60 (1991). Thus, the binding molecules which target these antigens, whether used in separate conjugates or in combination with conjugates which include anti-CD3 binding molecules, may be conjugated to microbeads or polymers and used as conjugates of the invention. Some of these antigens, such as CD2, CD4, CD5, and CD8 are specifically expressed by T cells or subsets of T cells. Thus, in one embodiment of the invention, an anti-CD3 binding molecule and an anti-CD2, anti-CD4, anti-CD5, anti-CD8, anti-CD28 or other binding molecule specific for T cells, is conjugated to a polymer backbone, a liposome, or a microbead. The polymerized or immobilized pairs of binding molecules can then be used to activate T cells in vivo, in humans or in other mammals.

It should be understood that the terms and expressions described herein are exemplary only and not limiting, and that the scope of the invention is defined only in the claims which follow, and includes all equivalents of the subject matter of those claims.

What is claimed is:

1. A method of increasing activation or proliferation of T cells in a non-human mammal without causing immunosuppression comprising administering a molecular conjugate having a polymer backbone or microbead coupled with a plurality of binding molecules which lack an Fc portion, each being specific for an antigen on a T cell.

2. The method of claim 1 wherein the antigen on the T cell is CD3, and the polymer backbone is a microbead.

3. The method of claim 2 wherein the microbead is a glutaraldehyde modified latex microbead.

4. The method of claim 1 wherein the binding molecule is selected from the group consisting of immunoglobulin, Fv, Fab, and F(ab')$_2$ fragments thereof.

5. A method of increasing the in vivo antibody response against an antigen comprising administering a molecular conjugate comprising a polymer backbone or microbead coupled with a plurality of binding molecules which lack an Fc portion, each being specific for an antigen on a non-human mammalian T cell.

6. The method of claim 5 wherein the antigen on the T cell is CD3, and the polymer backbone is a microbead.

7. The method of claim 6 wherein the microbead is a glutaraldehyde modified latex microbead.

8. The method of claim 5 wherein the binding molecule is selected from the group consisting of antibodies, Fv, Fab, and F(ab')$_2$ fragments thereof.

* * * * *